US008645956B2

(12) United States Patent
Becker et al.

(10) Patent No.: US 8,645,956 B2
(45) Date of Patent: Feb. 4, 2014

(54) METHOD AND COMPUTER SYSTEM FOR DESIGNING AND/OR PROVIDING COMPUTER-AIDED TASKS FOR MEDICAL TASK FLOWS

(75) Inventors: Detlef Becker, Möhrendorf (DE); Karlheinz Dorn, Kalchreuth (DE); Vladyslav Ukis, Nürnberg (DE); Hans-Martin Von Stockhausen, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 520 days.

(21) Appl. No.: 12/712,327

(22) Filed: Feb. 25, 2010

(65) Prior Publication Data

US 2010/0223617 A1 Sep. 2, 2010

(30) Foreign Application Priority Data

Feb. 27, 2009 (DE) .......................... 10 2009 010 889

(51) Int. Cl.
*G06F 9/46* (2006.01)
(52) U.S. Cl.
USPC .......................................... 718/100; 717/120
(58) Field of Classification Search
None
See application file for complete search history.

(56) References Cited

U.S. PATENT DOCUMENTS

| | | | | |
|---|---|---|---|---|
| 7,653,873 B2* | 1/2010 | Brandt et al. | ................. | 715/234 |
| 8,249,891 B2* | 8/2012 | Shen | ................. | 705/2 |
| 2002/0032582 A1* | 3/2002 | Feeney et al. | ................. | 705/2 |
| 2003/0206646 A1* | 11/2003 | Brackett | ................. | 382/128 |
| 2006/0101154 A1* | 5/2006 | Becker et al. | ................. | 709/236 |
| 2006/0206858 A1* | 9/2006 | Becker et al. | ................. | 717/104 |
| 2007/0074211 A1* | 3/2007 | Klug | ................. | 718/100 |
| 2007/0240108 A1* | 10/2007 | Dorn et al. | ................. | 717/114 |
| 2007/0283320 A1* | 12/2007 | Dorn et al. | ................. | 717/107 |
| 2008/0016466 A1* | 1/2008 | Grasser et al. | ................. | 715/835 |
| 2008/0082966 A1* | 4/2008 | Dorn et al. | ................. | 717/120 |
| 2008/0141213 A1* | 6/2008 | Dorn et al. | ................. | 717/100 |
| 2008/0141234 A1* | 6/2008 | Becker et al. | ................. | 717/162 |
| 2008/0141250 A1* | 6/2008 | Dorn et al. | ................. | 718/100 |
| 2009/0138318 A1* | 5/2009 | Hawkins et al. | ................. | 705/9 |
| 2010/0057828 A1* | 3/2010 | Hofmann et al. | ................. | 709/202 |

* cited by examiner

*Primary Examiner* — Emerson Puente
*Assistant Examiner* — Hiren Patel
(74) *Attorney, Agent, or Firm* — Harness, Dickey & Pierce, P.L.C.

(57) ABSTRACT

A method and a computer system are disclosed for designing and/or providing computer-aided tasks for medical task flows. In at least one embodiment, the method includes providing one or more tasks of at least one task flow, which can exchange data with one or a number of other tasks, in so far as they comply with at least one requirement for exchanging data; providing task flow management, which manages requirements in respect of a task and grants a task access for a task flow according to at least one of the requirements; providing at least one task container, which is made available as host for a task, in so far as the task complies with at least one requirement for access to the host; and providing at least one domain platform, which is used to convert the functionality and logic of at least one task, in so far as the task complies with at least one requirement in respect of the conversion.

14 Claims, 2 Drawing Sheets

METHOD AND COMPUTER SYSTEM FOR DESIGNING AND/OR PROVIDING COMPUTER-AIDED TASKS FOR MEDICAL TASK FLOWS

PRIORITY STATEMENT

The present application hereby claims priority under 35 U.S.C. §119 on German patent application number DE 10 2009 010 889.0 filed Feb. 27, 2009, the entire contents of which are hereby incorporated herein by reference.

FIELD

At least one embodiment of the invention generally relates to a method and/or a computer system for designing and/or providing computer-aided tasks for medical task flows.

BACKGROUND

The design of so-called medical tasks for clinical task flows (computer-aided work sequences) is not a standardized process at present. It generally involves analyzing the functionality required by the user, designing a corresponding technical concept and converting the designed concept using programming engineering.

The design of the technical concept also involves the important challenge of structuring the relevant medical task so that it:
  (a) can manage its lifecycle correctly
  (b) can be hosted in a so-called task container
  (c) can process entities from the medical domain appropriately
  (d) can exchange data with other tasks
  (e) can be connected to other tasks in a task flow.

Providing the above characteristics ensures that a task is robust and can be integrated in any task flows. Currently however only a few or no technical resources are available to ensure the characteristics.

As a result the following problems occur with tasks:
  problems with the hosting of tasks in a task container
  lack of support from medical standards
  lack of appropriate processing of medical entities and/or units
  problems with the data flow between tasks of a task flow
  problems with connecting tasks in a task flow Currently a specific implementation concept is designed for each task. The concept must ensure that the above-mentioned characteristics (a)-(e) of the task are complied with. However there are no resources for checking and enduring whether the respective concept complies with requirements.

Therefore problems with tasks such as applicability or runtime are only picked up in a late design phase. Eliminating the problems takes a great deal of time and is also uneconomical.

SUMMARY

In at least one embodiment of the invention, the abovementioned procedure is improved, particularly in respect of at least one of the abovementioned characteristics.

One aspect of at least one embodiment of the invention is a method for designing computer-aided tasks for medical task flows, comprising the following steps:
  providing one or more tasks of at least one task flow, which can exchange data with one or a number of other tasks, in so far as they comply with at least one requirement (IPort) for exchanging data,
  providing task flow management, e.g. CSM, which manages requirements e.g. ITask in respect of a task and grants a task access for a task flow according to at least one of the requirements,
  providing at least one task container, which is made available as host for a task, in so far as the task complies with at least one requirement, e.g. IContainer, for access to the host and
  providing at least one domain platform, which is used to convert the functionality and logic of at least one task, in so far as the task complies with at least one requirement, e.g. IDomain in respect of the conversion.

Preferably a task includes a so-called front end and a so-called back end. The functionality and process logic of a task can be made available in the back end and a presentation logic of the task can be made available in the front end.

In at least one embodiment of the invention, the front end is made available on one computer and the back end on another computer.

A requirement in respect of a task is realized expediently in both the front end and the back end.

A requirement for access to the host is realized expediently in both the front end and the back end.

A requirement for a data exchange is realized expediently in the back end.

A requirement in respect of a task functionality and logic conversion is realized expediently in the back end.

A further aspect of at least one embodiment of the invention is a computer system for providing computer-aided tasks for medical task flows, suitable in particular for implementing the method according to one of the preceding method steps, having
  means for providing one or more tasks of at least one task flow, which can exchange data with one or more other tasks, in so far as they comply with at least one requirement (IPort) for exchanging data,
  a task flow manager (CSM), which manages requirements (ITask) in respect of a task and grants a task access for a task flow according to at least one of the requirements,
  at least one task container, which is made available as host for a task, in so far as the task complies with at least one requirement (IContainer) for access to the host and
  at least one domain platform, which is used to convert the functionality and logic of at least one task, in so far as the task complies with at least one requirement (IDomain) in respect of the conversion.

A task here can consist of a so-called front end and a so-called back end, which can preferably be implemented on different computers.

One further aspect of at least one embodiment of the invention is a computer program product with computer program code for implementing the method steps of the inventive method, the computer program code being executed on a computer, in particular on the abovementioned computer system.

One further aspect of at least one embodiment of the invention is a computer program product of the above-mentioned type, characterized in that the computer program code is stored on a medium that can be read by a computer.

At least one embodiment of the invention is characterized by at least one of the following advantages:
  At least one embodiment of the invention simplifies task design by way of standardization and makes resulting tasks more robust.

At least one embodiment of the inventive method is also generic and can be used to design any medical task.

BRIEF DESCRIPTION OF THE DRAWINGS

An example embodiment of the invention is described in more detail below with reference to the drawings, in which.

DETAILED DESCRIPTION OF THE EXAMPLE EMBODIMENTS

Figure 1:
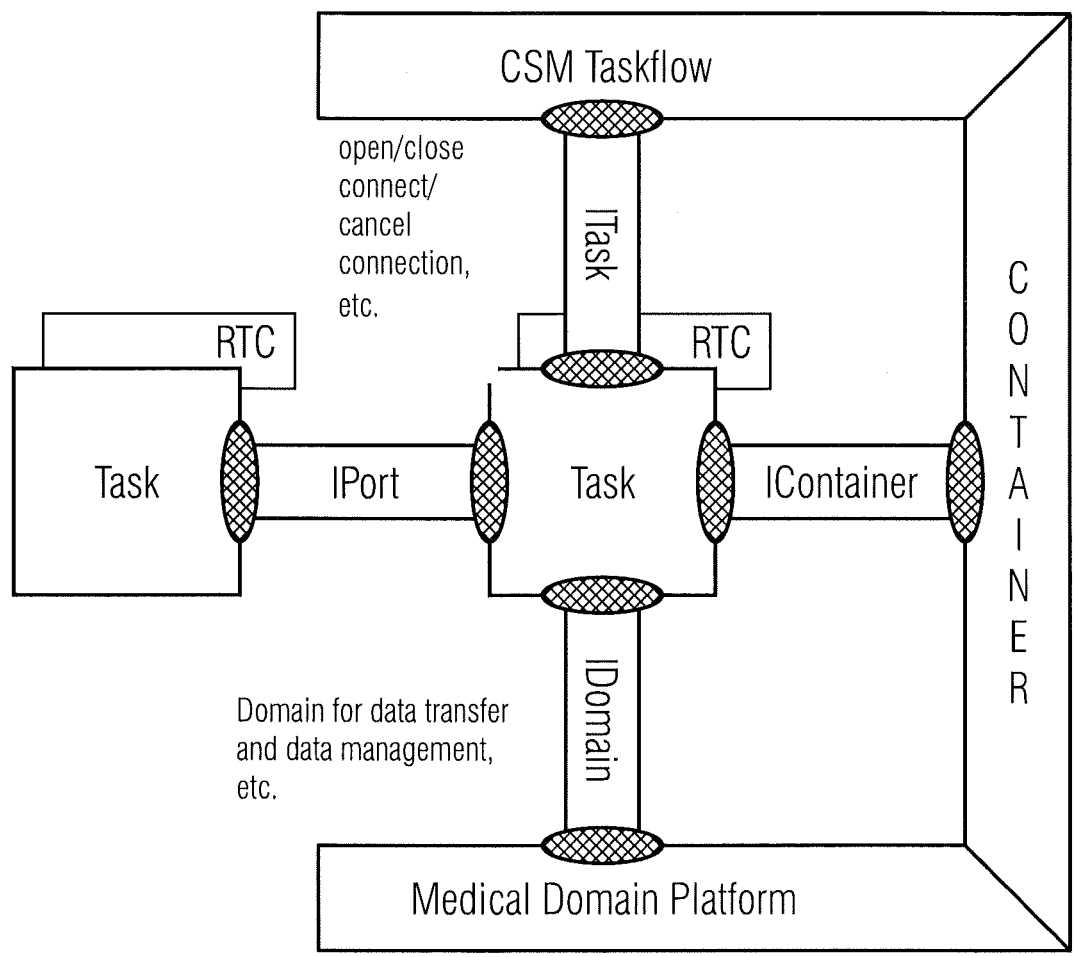
FIG. 1 shows so-called ITask, IContainer, IDomain and IPort contracts by way of example

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Task design can be standardized in that according to an embodiment of the invention a specifically defined environment is generated for a task, ensuring that the task complies with the characteristics (a)-(e) listed in the introduction.

This environment is shown by way of example in FIG. 1 and includes essentially three components: CSM Task Flow, Container and Medical Domain Platform.

The Central Strategy Manager (CSM) is able to execute task flows. It is accessible for a task by means of the so-called ITask contract (FIG. 1). This contract must be complied with by a task in order to be part of the CSM task flow.

The Task Container acts as host for a task. It is accessible for the task by means of the IContainer contract (FIG. 1).

The Medical Domain Platform in the lower region of FIG. 1 makes high abstractions available for the implementation of medical functionality in a task. The platform is accessible for the task by means of the IDomain contract.

A task must therefore comply with the ITask, IContainer and IDomain contracts in order to be able to operate in the environment shown in FIG. 1. The task should also comply with the IPort contract (on the left in FIG. 1) in order to be able to exchange data with other tasks of a task flow.

A task generally includes a front and back end component. The business logic or process logic of the task is implemented in the back end, while the presentation logic is covered in the front end. The front and back ends of the tasks are generally distributed physically over different computers.

The ITask contract should be complied with by both the front end and the back end of the task, so that the CSM can manage them as a whole. The IContainer contract must also be implemented by both the front end and back end of the task. A dedicated container is started respectively on the front end computer (RTC or Rich Thin Client in FIG. 1) and on the back end computer. Both containers are managed by the CSM.

The IDomain contract is also only complied with by the back end of a task, since the domain platform is only used to implement the business logic of the task. Finally the IPort contract is only complied with in the back end of the task to exchange data with other tasks. Since the data exchange only takes place in the back end, it is not essential to comply with the IPort contract in the front end of the task.

The following contracts to be complied with by a task are described in detail below: ITask, IContainer, IDomain and IPort.

a) ITask Contract

The ITask contract requires of a task the implementation of a specific protocol, allowing the CSM to manage the task so that it can operate in a task flow. Compliance with the ITask contract thus ensures that a task can be connected to other tasks by the CSM.

The ITask contract contains the following attributes, which are described point by point below:

The PortSupport interface is used by a task to access its ports. It allows the task to be notified when data arrives at a specific port. It also allows the task to route data to a specific port.

The Status interface is used by a task in the front end to access the Windows status bar.

The StepEngine interface allows a task to switch between its configured steps. A step is a collection of components (presentation and business components), which are loaded and unloaded by the StepEngine. It is possible to switch between the steps in the configuration sequence.

The StepSupport interface is also available in addition to the StepEngine interface for step management.

The WorkflowSupport interface is implemented by a task (front and back end) to be part of the CSM task flow.

b) IContainer Contract

The IContainer contract makes the following so-called container services available for the task:

| | |
|---|---|
| syngo.Common.Core.IUserData | Provides access to the attributes defined in the Provides access in Presentation and Business Forms. |
| syngo.Common.Core.TaskInformation.ItaskflowModelService | Provides access to the Task Flow Information Model of the CSM. |
| syngo.Common.Controls.WinForms.IStatus | Interface with an access node for status representation e.g. within a status profile. |
| syngo.Common.Core.IShutdownService | This interface is used to inform a task of a so-called shutdown. It is also possible to reject the shutdown (if it is not a mandatory shutdown). This service can only be accessed by task front ends. |
| syngo.Common.Services.Workplace-Management.IWorkplaceManager | The management interface with the local or remote operating environment supports: Requests for management information e.g. available devices and monitors etc. The setting of characteristics for management objects, e.g. environment variables, Registration for management events e.g. message, if the management object is manipulated. |
| syngo.Common.Core.IUserContextService | Provides information about current user authentications. Users can change profiles. |
| syngo.Common.Container.Workplace-Management.DisplayDevices.IDeviceManager | Provides lists of available monitors inter alia. |
| syngo.Common.Core.IToolManagement | Is used by a task of a so-called control environment. Allows so-called service contracts to be registered or made available on the server side. |
| syngo.Common.Core.IControlArea | Interface for interaction with a control image environment. Is used by a task of a so-called control environment. |

The CommunicationClient interface is used by the front end of a task to communicate with its back end.

The CommunicationServer interface is used by the back end of a task to communicate with its front end.

The Form interface is used by a task to manage its front and back end components, which are realized as forms (presentation and business form).

The PluginManagement interface is used by a task to load and unload its plugins dynamically.

The PopupManagament interface is used by a task in the front end to manage popup windows.

These services must be used by a task in order to be able to interact correctly with its environment shown in FIG. 1.

c) IDomain Contract

The IDomain contract is made available to the task in order to implement medical functionality quickly. This contract includes individual so-called business components (BC), which cover parts of the medical domain, e.g. imaging, transfer, data management etc. The business components ensure that the tasks implement medical standards such as DICOM, HL7 etc. correctly. They include interfaces such as DicomDeviceNodesBC for a DICOM configuration, BasicTransferBC for one or more data transfers, BasicDataBC for data management, BasicWorkflowBC for workflow management, BasicImagingBC for calculating and displaying medical images, BasicLayoutBC for creating layouts for displaying the medical images, BasicReportingBC for creating medical reports, BasicResultsBC for managing so-called evidence documents for medical reports and BasicPrintingBC printing out the data.

d) IPort Contract

The IPort contract must be used by a task in order to exchange data with other tasks of a task flow. The contract provides the following attributes:

| | |
|---|---|
| Connections | Port connection to other ports |
| DataRoles | Data role suitable for port |
| FullName | Full name |
| IsInputPort | Display when an input port is active |
| IsOutputPort | Display when an output port is active |
| IsPublishedToClinicalTask | Public domain for clinical task |
| IsSecondaryDataPort | Second data port |
| Name | Port name |

A task receives input data about its input ports and sends the result data to other tasks by way of its output ports.

e) Task Compliance Checker

Figure 2:
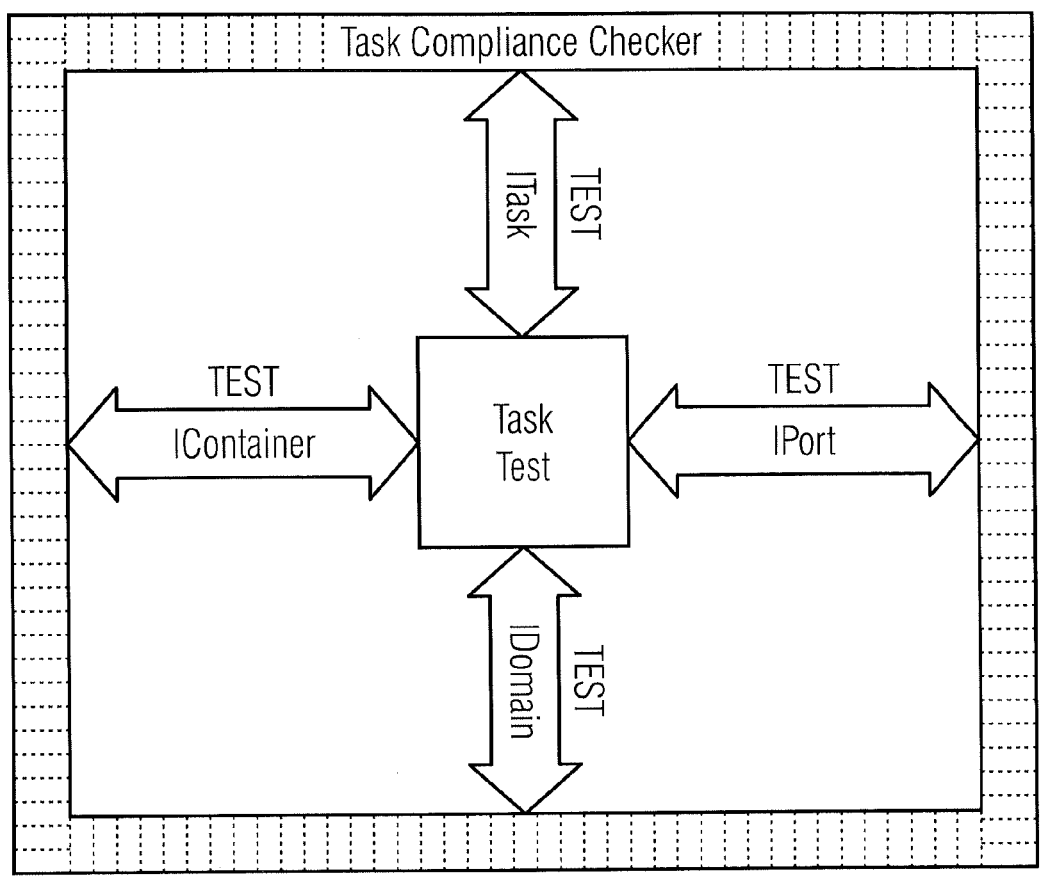
FIG. 2 shows a verification of task compatibility by way of example.

To ensure that a task complies with the ITask, IContainer, IDomain and IPort contracts shown in FIG. 1, in addition to the contracts (see a) to d)) a so-called Task Compliance Checker (TCC) is also made available to the task designers, as shown in FIG. 2.

The TCC is able to instantiate a task in a "standalone" manner (i.e. without CSM, Container, Domain Platform and other tasks) and automatically test whether it complies with the abovementioned four infrastructure contracts (see FIG. 2).

The TCC supplies the task designer with information about whether the relevant task complies with the four contracts before it operates in a productive environment with CSM, Container, Medical Domain Platform and other tasks (FIG. 1). It essentially contributes to stable and reliable tasks for the productive environment.

An embodiment of the invention is characterized by the following advantages:
  Standardization of task design by specifying the ITask, IContainer, IDomain and IPort contracts which have to be complied with by the tasks
  Reducing task design costs
  Reducing errors when designing task implementation concepts
  Accelerated task design becomes possible
  Ensuring the hosting of a task in a container by specifying the IContainer contract
  Simple support of medical standards and appropriate processing of medical entities by tasks by using the IDomain contract
  Ensuring the data flow between tasks of a task flow by complying with the IPort contract
  Ensuring the option of connecting a task to other tasks by complying with the ITask contract
  Option of testing a task separately for compliance with the ITask, IContainer, IDomain and IPort contracts, without having to run a productive process environment with CSM, Container, Medical Domain Platform and other tasks—Task Compliance Checker
  Reducing test times and costs
  Improving capacity of task for testing
  Increasing task robustness The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for designing one or more computer-aided tasks for at least one medical task flow executable by a central strategy manager (CSM) in a system including a front end device and a back end device, the method comprising:
   providing the one or more of the computer-aided tasks of the at least one medical task flow, configured to exchange data with other tasks, in so far as the other tasks comply with at least one port requirement, specified in a port contract negotiated between the tasks and the CSM, for exchanging data with the other tasks over ports specified in the port contract;
   providing task flow management, to manage task requirements, specified in a task contract negotiated between the tasks and the CSM, in respect of a task and to grant a task access for the medical task flow, if the task utilizes interfaces that comply with protocols specified by the task requirements;
   providing at least one task container, made available as host for a task, in so far as the task complies with at least one container requirement, specified in a container contract negotiated between the tasks and the CSM, for access to the host using services specified in the container contract; and
   providing at least one domain platform, to convert functionality and logic of at least one task such that the at least one task complies with at least one medical standard being implemented by the at least one medical task flow, in so far as the at least one task complies with at least one domain requirement, specified in a domain contract negotiated between the tasks and the CSM, in respect of the conversion, the functionality and logic being at least one of medical imaging, data transfer, and data management,
      wherein the functionality and process logic of the at least one task are implemented in the back end device and presentation logic of the at least one task is implemented in the front end device.

2. The method as claimed in claim 1, wherein a requirement in respect of the at least one task is realized in both the front end device and the back end device.

3. The method as claimed in claim 2, wherein a requirement for access to the host is realized in both the front end device and the back end device.

4. The method as claimed in claim 3, wherein a requirement for a data exchange is realized in the back end device.

5. The method as claimed in claim 4, wherein a requirement in respect of a task functionality and logic conversion is realized in the back end device.

6. The method as claimed in claim 1, executed by a computer performing a computer program implementing the method.

7. A computer system for providing one or more computer-aided tasks for at least one medical task flow executable by a central strategy manager (CSM) in a system including a front end device and a back end device, the system comprising:
   means for providing the one or more of the computer aided tasks of the at least one medical task flow, configured to exchange data with other tasks, in so far as the other tasks comply with at least one port requirement, specified in a port contract negotiated between the tasks and the CSM, for exchanging data with the other tasks over ports specified in the port contract;
   a task flow manager to manage task requirements, specified in a task contract negotiated between the tasks and the CSM, in respect of a task and to grant a task access for the medical task flow, if the task utilizes interfaces that comply with protocols specified by the task requirements;
   at least one task container, made available as host for a task, in so far as the task complies with at least one container requirement, specified in a container contract negotiated between the tasks and the CSM, for access to the host using services specified in the container contract; and
   at least one domain platform, usable to convert functionality and logic of at least one task such that the at least one task complies with at least one medical standard being implemented by the at least one medical task flow, in so far as the at least one task complies with at least one domain requirement, specified in a domain contract negotiated between the tasks and the CSM, in respect of the conversion, the functionality and logic being at least one of medical imaging, data transfer, and data management,
      wherein the functionality and process logic of the at least one task are implemented in the back end device and presentation logic of the at least one task is implemented in the front end device.

8. The computer system as claimed in claim 7, wherein a requirement in respect of the at least one task is realized in both the front end device and the back end device.

9. The computer system as claimed in claim 7, wherein a requirement for access to the host is realized in both the front end device and the back end device.

10. The computer system as claimed in claim 7, wherein a requirement for a data exchange is realized in the back end device.

11. The computer system as claimed in claim 7, wherein a requirement in respect of a task functionality and logic conversion is realized in the back end device.

12. A computer program product, wherein a computer program implementing the method as claimed in claim 1 is stored on a non-transitory computer readable storage medium.

13. A computer system for providing one or more computer-aided tasks for at least one medical task flow executable by a central strategy manager (CSM) in a system including a front end device and a back end device, the task flow configured to exchange data with other tasks, in so far as the other tasks comply with at least one port requirement, specified in a port contract negotiated between the tasks and the CSM, for exchanging data with the other tasks over ports specified in the port contract, the system comprising:
   a processor and a non-transitory computer readable medium, the computer system configured to execute,
   a task flow manager to manage task requirements, specified in a task contract negotiated between the tasks and the CSM, in respect of a task and to grant a task access for the medical task flow, if the task utilizes interfaces that comply with protocols specified by the task requirements;

at least one task container, made available as host for a task, in so far as the task complies with at least one container requirement, specified in a container contract negotiated between the tasks and the CSM, for access to the host using services specified in the container contract; and at least one domain platform to convert functionality and logic of at least one task such that the at least one task complies with at least one medical standard being implemented by the at least one medical task flow, in so far as the at least one task complies with at least one domain requirement, specified in a domain contract negotiated between the tasks and the CSM, in respect of the conversion, the functionality and logic being at least one of medical imaging, data transfer, and data management, wherein the functionality and process logic of the at least one task are implemented in the back end device and presentation logic of the at least one task is implemented in the front end device.

14. A non-transitory computer readable storage medium including program segments for, when executed on a computer device, causing the computer device to implement the method of claim 1.

* * * * *